(12) United States Patent
Leyva et al.

(10) Patent No.: US 6,663,392 B2
(45) Date of Patent: Dec. 16, 2003

(54) SEQUENTIAL REASONING TESTING SYSTEM AND METHOD

(75) Inventors: Laura Leyva, San Antonio, TX (US); David Tulsky, Summit, NJ (US)

(73) Assignee: The Psychological Corporation, San Antonio, TX (US)

( * ) Notice: Subject to any disclaimer, the term of this patent is extended or adjusted under 35 U.S.C. 154(b) by 0 days.

(21) Appl. No.: 10/123,037

(22) Filed: Apr. 15, 2002

(65) Prior Publication Data

US 2003/0060729 A1 Mar. 27, 2003

(Under 37 CFR 1.47)

Related U.S. Application Data

(60) Provisional application No. 60/285,950, filed on Apr. 24, 2001.

(51) Int. Cl.[7] .............................................. G09B 19/00
(52) U.S. Cl. ...................................................... 434/236
(58) Field of Search ................................ 434/236, 237, 434/238

(56) References Cited

U.S. PATENT DOCUMENTS

| | | | |
|---|---|---|---|
| 1,139,256 A | | 5/1915 | Clark |
| 3,543,418 A | | 12/1970 | Press |
| 5,017,142 A | * | 5/1991 | Bemis et al. ................ 434/220 |
| 5,533,902 A | | 7/1996 | Miller |
| 5,911,581 A | | 6/1999 | Reynolds et al. |
| 6,030,226 A | | 2/2000 | Hersh |
| 6,053,739 A | * | 4/2000 | Stewart et al. ............... 434/236 |
| 6,159,014 A | * | 12/2000 | Jenkins et al. .............. 434/169 |
| 6,306,086 B1 | * | 10/2001 | Buschke ..................... 600/300 |

* cited by examiner

Primary Examiner—John Edmund Rovnak
(74) Attorney, Agent, or Firm—Allen, Dyer, Doppelt, Milbrath & Gilchrist, P.A.

(57) ABSTRACT

A method for testing a working memory of a subject includes the steps of presenting to a subject a first representation of a plurality of items and asking the subject to select a first item from the first representation. Next the subject is presented with a second representation of the plurality of items and is asked to select a second item from the second representation, the second item different from the first item. These steps test a subject's ability to select a different item from a plurality thereof, a first type of information. As a next aspect of the test the subject is asked to recall an order of the selected items. This step requires the subject to track the order of selection, another type of information. This juxtaposition of testing aspects increases the working memory load on the subject.

25 Claims, 6 Drawing Sheets

SEQUENTIAL REASONING TESTING SYSTEM AND METHOD

CROSS-REFERENCE TO RELATED APPLICATION

This application claims priority to provisional application No. 60/285,950, "Sequential Reasoning Testing System and Method," filed Apr. 24, 2001.

BACKGROUND OF THE INVENTION

1. Field of the Invention

The present invention relates to systems and methods for testing intelligence, and, more particularly, to such system and methods for testing working memory and/or fluid reasoning.

2. Description of Related Art

Tests are known in the art for testing a subject's ability to fill in a pattern of images, including those that present a series of images to the subject for subsequent filling in one of a plurality of other images (Clark, U.S. Pat. No. 1,139,256), complete a pattern (Press, U.S. Pat. No. 3,543,418), or perform a matching task (Miller, U.S. Pat. No. 5,533,902; Reynolds et al., U.S. Pat. No. 5,911,581; Hersh, U.S. Pat. No. 6,030,226).

However, there are no tests known in the art that also require an additional memory dimension imposed by removing presented images sequentially.

SUMMARY OF THE INVENTION

It is therefore an object of the present invention to provide a system and method for testing a subject's working memory.

It is a further object to provide such a system and method for testing fluid reasoning.

It is another object to provide such a system and method for testing a combination of working memory and fluid reasoning.

It is also an object to provide such a system and method that provide for adaptive administration.

It is an additional object to provide a method for administering such a test.

It is yet a further object to provide a series of representations for use in such a test.

These and other objects are achieved by the present invention, a method for testing a working memory and fluid reasoning of a subject. The method comprises the step of sequentially presenting to a subject a first plurality of images. Each image is positioned in a different sector of a display device. The first plurality of images totals one fewer than a total number of sectors.

Next the subject is simultaneously presented with a second plurality of images. One of the second plurality of images bears an analogous relationship to the first plurality of images.

The subject is then asked to select an analogous image from the second plurality of images.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1A:
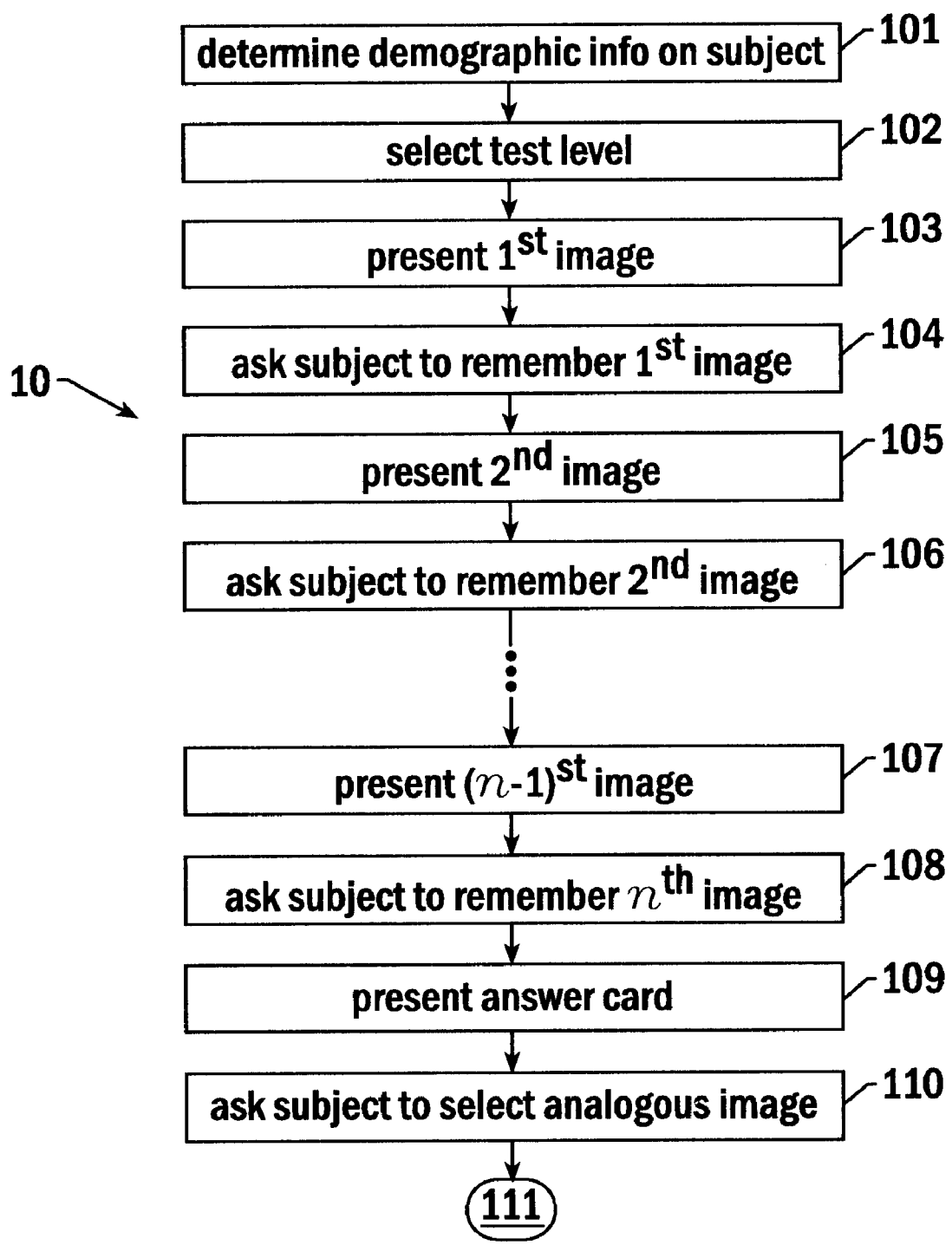
FIGS. 1A,1B is a flowchart outlining an administration of the test of the present invention.
Figure 1B:
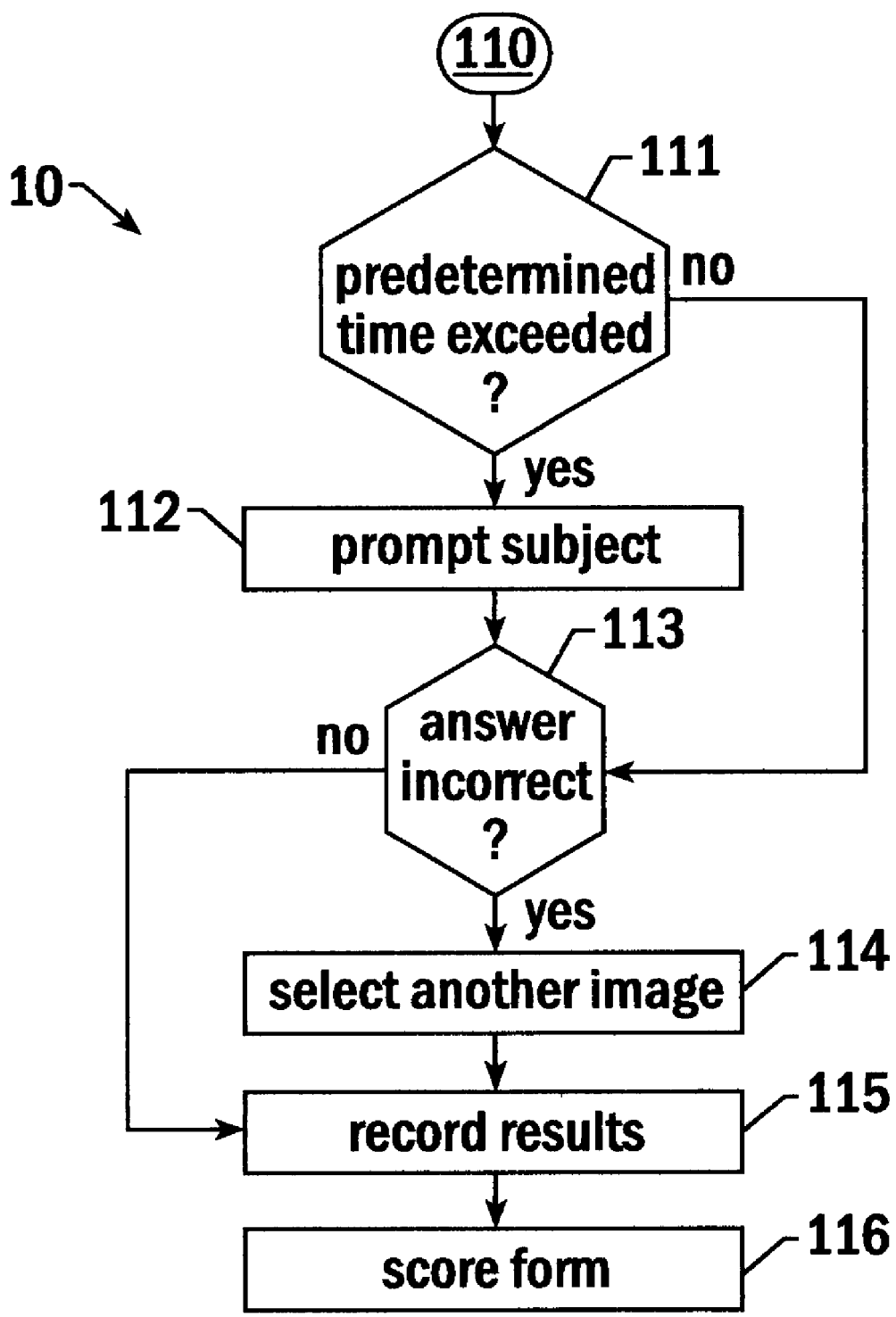

A description of the preferred embodiments of the present invention will now be presented with reference to FIGS. 1A–3B.

An exemplary flowchart of the test administration method (FIGS. 1A,1B) outlines steps to be taken in giving the working memory and fluid reasoning test 10 for presentation to a subject 20. The method comprises the steps of determining demographic information on the subject 20 (block 101) for the purpose of choosing an appropriate test level (block 102) to be presented. Such demographic information typically includes, but is not intended to be limited to, the subject's age and/or grade level.

Next the subject 20 is presented with a first representation of one of a first plurality of images (block 103). In a first embodiment, this first representation comprises a card or sheet of paper with a matrix of sectors, here four 31–34, thereon, with one of the sectors having a first image therein. An exemplary first representation 30 is given in FIG. 2A, wherein an image 35 of four dots is shown as being positioned within a first sector 31. Sectors 32–34 are blank. Next the subject 20 is asked to look at the first image 35 and remember it (block 104).

The subject 20 is then presented with a second representation 40 of a second of the first plurality of items (FIG. 2B, block 105), with a second image 36 of a square in the second sector 32. Sectors 31,33,34 are blank. The subject 20 is then asked to look at the second image 36 and remember it (block 106).

This process is repeated n–1 times (blocks 107–108), where n is the number of sectors on the matrix. Here, n=4, and thus the third presentation 50 is the final one, with a pentagonal figure 37 shown in sector 33 (FIG. 2C), and sectors 31,32,34 are blank. It is obvious to one of skill in the art that n may equal any reasonable number, with n typically an even integer; 4 and 6 are typical numbers.

When all representations 30,40,50 have been viewed, the subject 20 is presented with an nth, here a fourth, representation 60 (FIG. 2D) on an "answer card" 66 (block 109) and is asked to select an analogous image from a second plurality of images 61–65 (block 110). The second plurality of images may comprise a reasonable number from which to choose, typically 4 or 5, although this is not intended as a limitation.

In the test comprising representations as shown in FIGS. 2A–2D, the correct choice would be image 61. If a predetermined time 19 is exceeded by the subject 20 in making a selection (block 111), prompting is given by the test giver 21 (block 112). If an incorrect answer is given (block 113), the subject 20 is asked to select another image from the second plurality of images (block 114). Once the test 10 has been completed and recorded on form 29 (block 115), the form is scored (block 116). The score is indicative of a working memory and fluid reasoning ability of the subject 20.

Figure 2A:
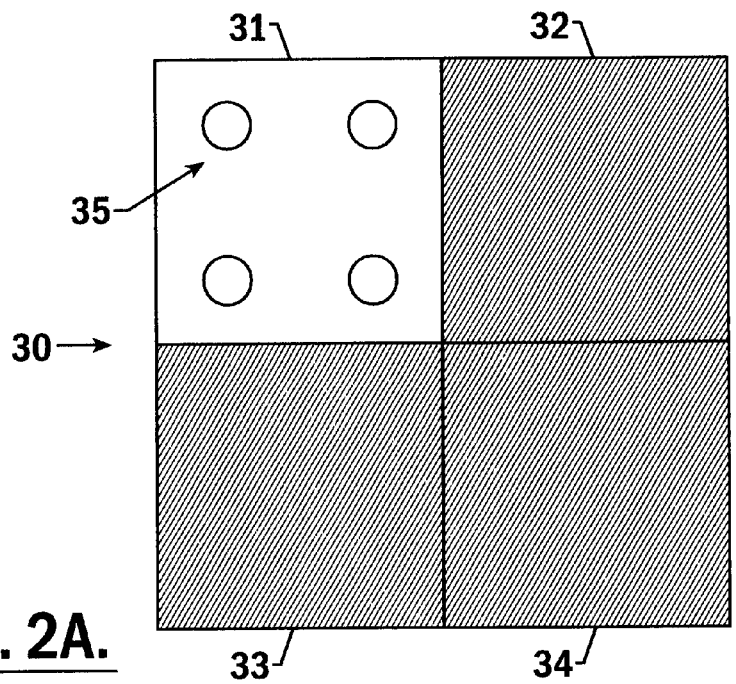
FIGS. 2A–2D is an exemplary series of image cards, including three image cards (FIGS. 2A–2C) and an answer selection card (FIG. 2E).
Figure 2B:
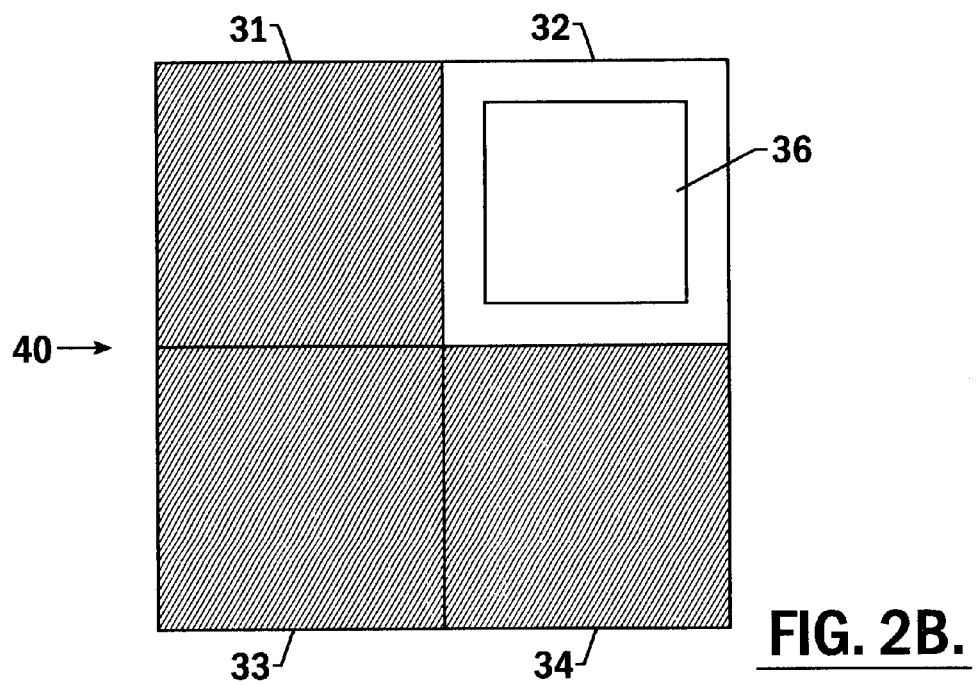
Figure 2C:
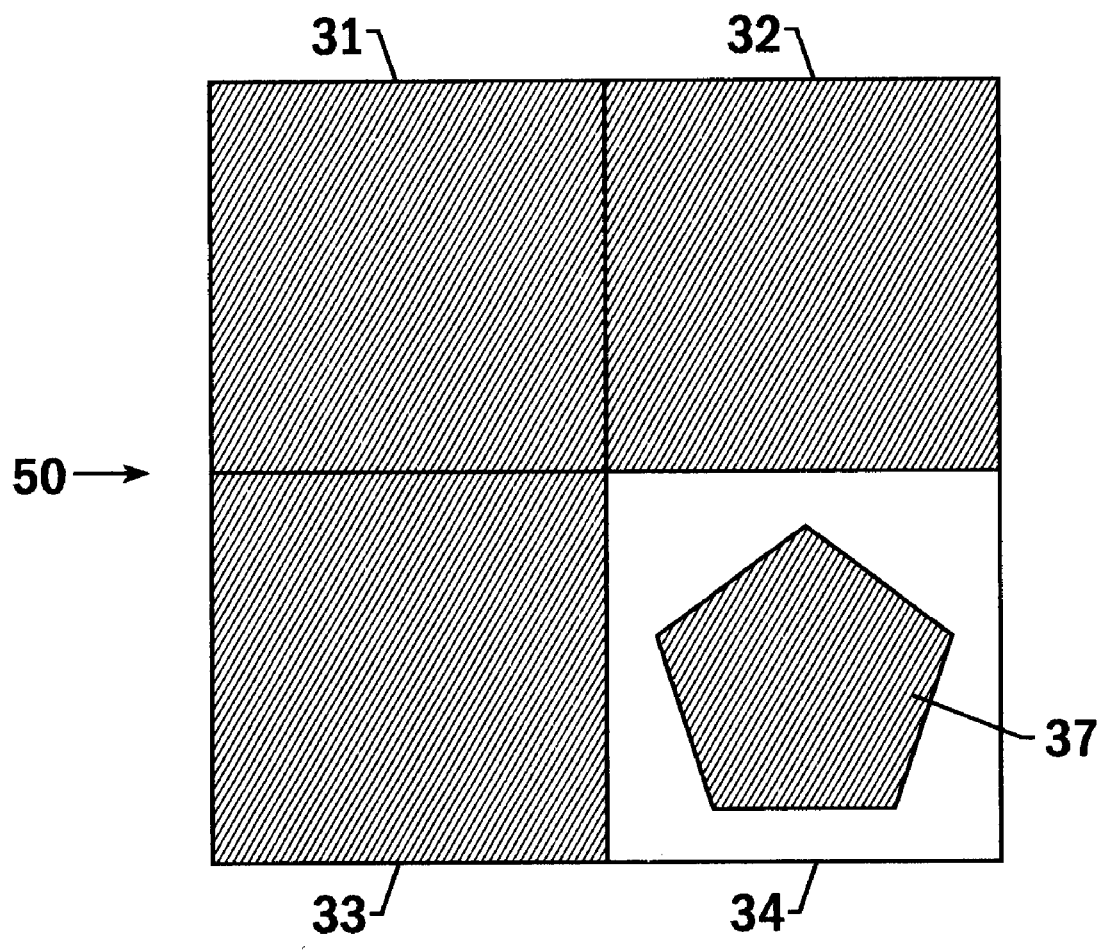
Figure 2D:
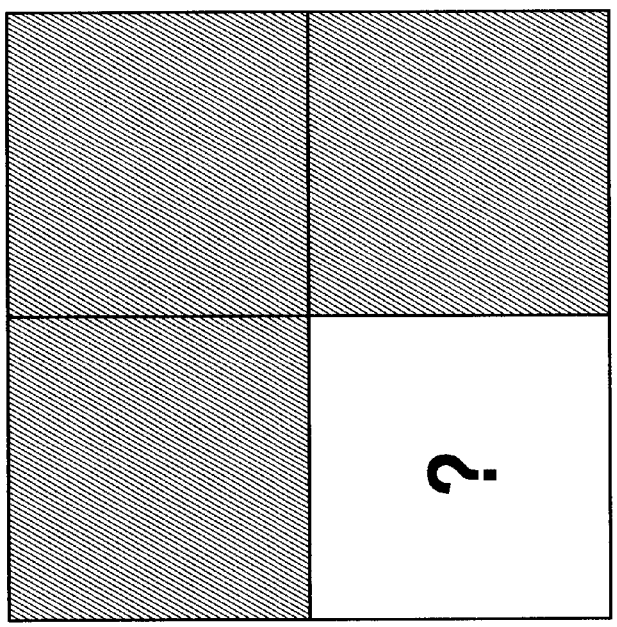
Figure 2D:
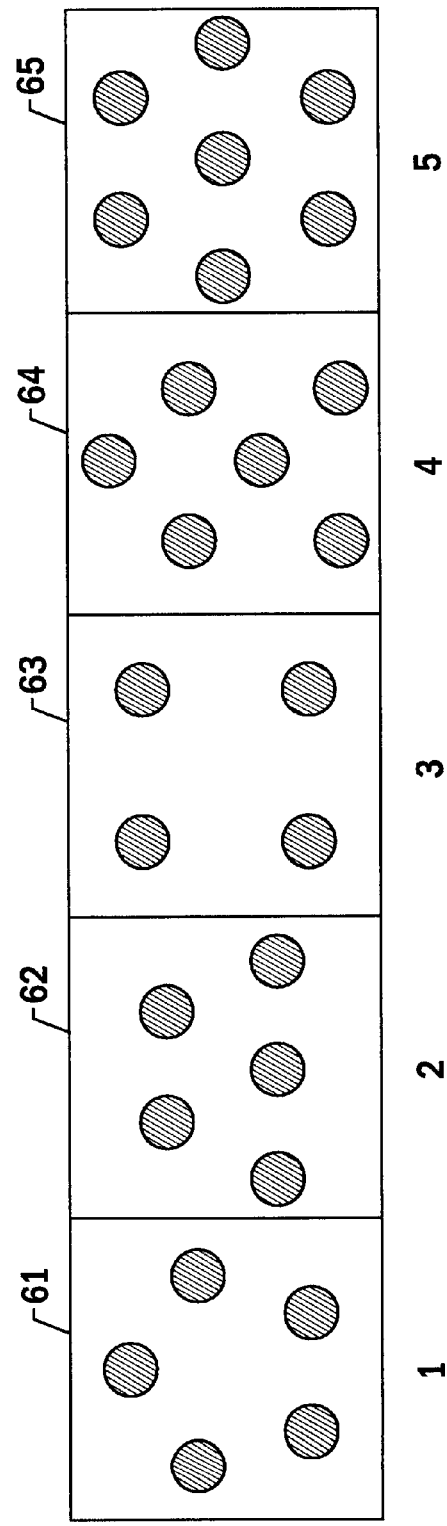

One of skill in the art will recognize that a "manual" or "automated" test administration mode may be contemplated. In a manual mode (FIG. 3A), picture cards 30,40,50 such as those illustrated in FIGS. 2A–2C and an answer representation card 60 such as that illustrated in FIG. 2D are shown to the subject 20 by a human test giver 21, who also manually records the times 19 and responses on a form 29. Scoring may be done either by the test giver 21 or by another entity, such as a testing corporation or computer.

In an automated embodiment (FIG. 3B), the "test giver" comprises a computer 22 having resident thereon a software package 23 adapted to give the test in substantially the same steps as listed above. In communication with and under direction from the computer 22 is a display screen 24, on which may be presented the representations and which, using a keyboard 31 or a pointing device such as a mouse 25 in communication with the computer 22, the subject 20 may make selections. Other forms of receiving communication from the subject 20 may comprise such devices known in the art as a touch screen or a microphone for voice recognition and translation, and the invention is not intended to be limited to particular input/output devices.

The computer 22 further comprises a clock 26 accessible by the software 23 for performing the timing functions. In this automated case, the prompting and asking steps can be performed by displaying a statement or query on the screen 24, or via a speaker 27 in communication with the computer 22, under direction of the software 23.

Scoring in this case could be performed by the software 23 resident in the computer 20. Alternatively, the digital "scoring form," a data record, may be transmitted via modem 28 to a scoring center 80 remote from the test site 11.

Figure 3A:
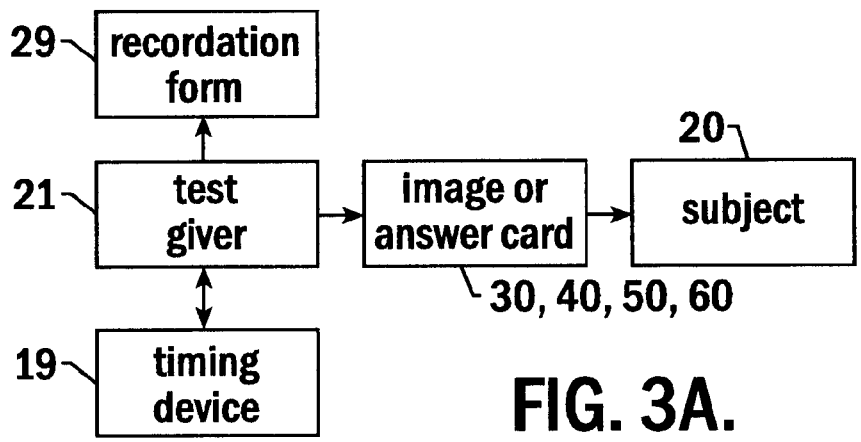
FIGS. 3A,3B are schematic diagrams of a manual (FIG. 3A) and an automated (FIG. 3B) system for administering a test.
Figure 3B:
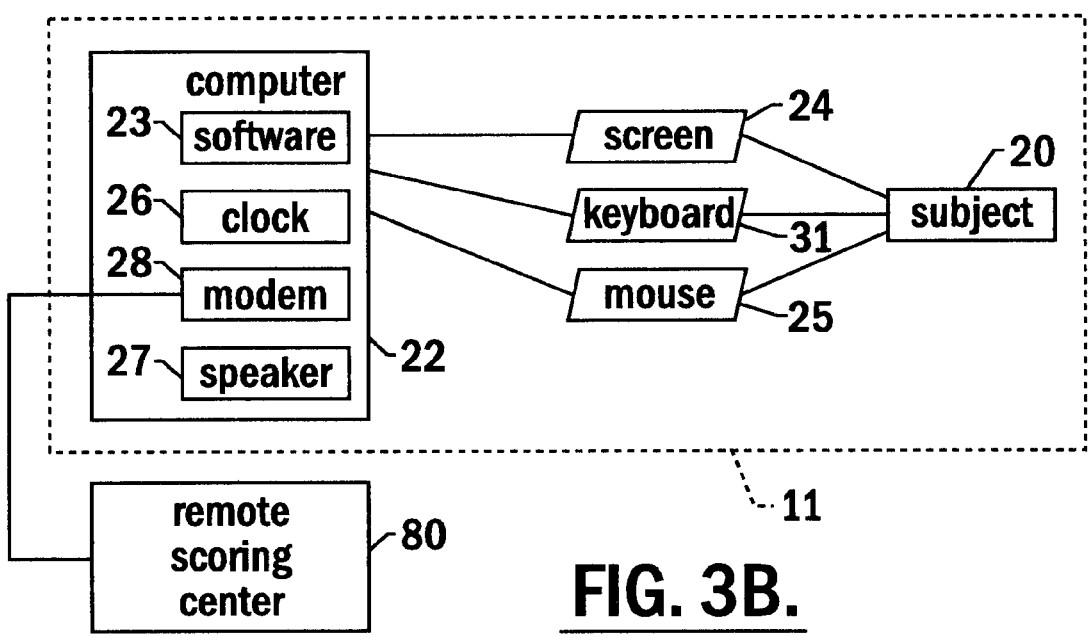

Another benefit of the automated embodiment of FIG. 3B is an ability to perform an adaptive administration of a test. In this case a contemporaneous evaluation of the subject 20 occurs during the test administration, and the software 23 adjusts the presentation of subsequent images based upon the results of previous portions of the test.

It may be appreciated by one skilled in the art that additional embodiments may be contemplated, including alternate representations of items and alternate modes of presenting the items to a subject.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for testing a working memory and fluid reasoning of a subject, the method comprising the steps of:
   sequentially presenting to a subject a first plurality of images, each image positioned in a different sector of a display device, the first plurality of images totaling one fewer than a total number of sectors;
   simultaneously presenting to the subject a second plurality of images, one of the second plurality of images bearing an analogous relationship to the first plurality of images; and
   asking the subject to select an analogous image from the second plurality of images.

2. The method recited in claim 1, further comprising the step of receiving a response from the subject.

3. The method recited in claim 2, further comprising the step of timing an interval between the second plurality of images presenting step and the response receiving step.

4. The method recited in claim 3, further comprising the step of prompting the subject if a predetermined time has been exceeded without receiving a response.

5. The method recited in claim 2, further comprising the step, if the received response is incorrect, of indicating that the response was incorrect, and asking the subject to select another image from the second plurality of images.

6. The method recited in claim 2, further comprising the step of recording the response on a scoring form.

7. The method recited in claim 6, further comprising the step, following the asking step, of scoring the scoring form to determine a working memory and fluid reasoning indicator.

8. The method recited in claim 1, wherein the first plurality of images comprises three or five images, and wherein the second plurality of images comprises four or five images.

9. The method recited in claim 1, wherein the first plurality of images presenting step comprises sequentially presenting the first plurality of images at predetermined intervals.

10. The method recited in claim 1, wherein the display device comprises a substantially planar matrix comprising the sectors.

11. The method recited in claim 10, wherein the display device comprises a sheet of paper having a matrix thereon.

12. The method recited in claim 10, wherein the display device comprises a display screen adapted to display a matrix.

13. The method recited in claim 1, further comprising the steps of determining a demographic indicator of the subject and selecting a first and a second plurality of images commensurate with the demographic indicator.

14. A system for testing a working memory and fluid reasoning of a subject, the system comprising:
   discrete representations of each of a first plurality of images, each image positioned in a different sector of a matrix, the first plurality of images totaling one fewer than a total number of sectors;
   an answer representation comprising a second plurality of images and the matrix, the matrix having sectors without images from the first plurality of images therein, one of the second plurality of images comprising a correct response image bearing an analogous relationship to the first plurality of images; and
   means for asking the subject to select an analogous image from the second plurality of images.

15. The system recited in claim 14, wherein the matrix further comprises an indicium in a sector corresponding to the sector not occupied by one of the first plurality of images, the indicium indicative of a location designated for the correct response image.

16. The system recited in claim 14, further comprising means for timing the asking step.

17. The system recited in claim 16, further comprising means for receiving a response from the subject.

18. The system recited in claim 17, further comprising means for prompting the subject if a predetermined time has been exceeded without receiving a response.

19. The system recited in claim 17, further comprising a scoring form.

20. The system recited in claim 19, further comprising means for scoring the scoring form to determine a working memory and fluid reasoning indicator.

21. The system recited in claim 16, further comprising means for indicating to the subject if an incorrect response has been received and for asking for another response.

22. The system recited in claim 16, wherein the discrete representations and the answer representation each comprises a sheet having a matrix divided into sectors thereon.

23. A system for testing a working memory of a subject, the system comprising:

a processor;

a display screen and an input device, each in electronic communication with the processor; and software means resident in the processor adapted to:

display to a subject discrete representations of each of a first plurality of images on the screen, each image positioned in a different sector of a matrix, the first plurality of images totaling one fewer than a total number of sectors;

display to the subject an answer representation comprising a second plurality of images and the matrix on the screen, the matrix having sectors without images from the first plurality of images therein, one of the second plurality of images comprising a correct response image bearing an analogous relationship to the first plurality of images; and ask the subject to select an analogous image from the second plurality of images; and receive from the subject a response via the input device.

24. The system recited in claim 23, wherein:

the processor comprises a clock; and the software means is further adapted to calculate and record a time difference between a displaying of the answer representation and an entry of a response.

25. The system recited in claim 24, wherein the software means is adapted to display a prompt if the time difference exceeds a predetermined time limit.

\* \* \* \* \*